United States Patent [19]

Dobson et al.

[11] 4,036,842

[45] July 19, 1977

[54] PROCESS FOR PREPARING POLYCYCLIC HETEROCYCLES HAVING A PYRAN RING

[75] Inventors: Thomas A. Dobson; Leslie G. Humber, both of Dollard des Ormeaux; Christopher A. Demerson; Ivo L. Jirkovsky, both of Montreal, all of Canada

[73] Assignee: American Home Products Corporation, New York, N.Y.

[21] Appl. No.: 613,160

[22] Filed: Sept. 15, 1975

Related U.S. Application Data

[63] Continuation-in-part of Ser. No. 311,023, Nov. 30, 1972, abandoned, which is a continuation-in-part of Ser. No. 289,714, Sept. 15, 1972, Pat. No. 3,939,178, which is a continuation-in-part of Ser. No. 148,895, June 1, 1971, Pat. No. 3,843,681.

[30] Foreign Application Priority Data

May 16, 1972 South Africa ............... 72/3344

[51] Int. Cl.² ............... C07D 491/14; C07D 491/22
[52] U.S. Cl. ............... 260/293.58; 260/293.57; 260/289 D; 260/294.8 B; 260/294.8 C; 260/296 T; 260/297 T; 260/297 B; 260/326.12 R; 260/326.16; 260/326.29; 260/326.5 SA; 260/326.5 B; 260/330.5; 260/332.2 A; 260/332.3 P; 260/345.2; 260/345.3; 424/263; 424/267; 424/274

[58] Field of Search ............... 260/293.57, 293.58, 260/296 T, 326.5 B, 330.5, 345.2, 326.29, 326.5 SA

[56] References Cited

FOREIGN PATENT DOCUMENTS 2,051,496    4/1971    Germany

OTHER PUBLICATIONS

Rieche et al., Chem. Ber. 89, pp. 1254–1262 (1956).
Warren et al., J. Am. Chem. Soc. 79, pp. 3812–3815 (1957).

*Primary Examiner*—Natalie Trousof
*Attorney, Agent, or Firm*—Stephen Venetianer

[57] ABSTRACT

A process applicable to the preparation of a wide variety of novel polycyclic heterocycles having a newly formed pyran ring is disclosed. According to the process an aromatic nucleus bearing an ethanol group, for example, 3,4-dimethoxyphenethyl alcohol, is condensed with an aldehyde or ketone or a protected aldehyde or ketone, for example, aminoactaldehyde diethyl acetal, in the presence of an acid catalyst to afford the polycyclic heterocycle, for example, 6,7-dimethoxy-l-isochromanmethylamine. The new heterocycles so formed are useful for preparing derivatives having antiinflammatory, antibacterial or antifungal activities.

11 Claims, No Drawings

PROCESS FOR PREPARING POLYCYCLIC HETEROCYCLES HAVING A PYRAN RING

CROSS-REFERENCES TO RELATED APPLICATIONS

This application is a continuation-in-part of our earlier filed application Ser. No. 311,023, filed Nov. 30, 1972, abandoned which is a continuation-in-part of our earlier filed application, Ser. No. 289,714, filed Sept. 15, 1972, U.S. Pat. No. 3,939,178 which is a continuation-in-part of our earlier filed application, Ser. No. 148,895, filed June 1, 1971, U.S. Pat. No. 3,843,681.

BACKGROUND OF THE INVENTION

This invention relates to a process for preparing intermediates which are useful for the subsequent preparation of compounds having pharmacologic activity. The intermediates are prepared by the hitherto undisclosed process described in the applications cited above. Furthermore, it should be noted that a number of these intermediates have an additional utility in that they, themselves, possess pharmacologic activities.

SUMMARY OF THE INVENTION

More particuarly, the useful intermediates of this invention of formula I are schematically represented by FIG. 1,

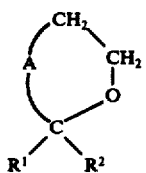   I.

in which A is

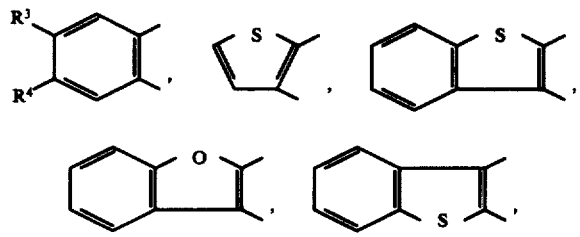

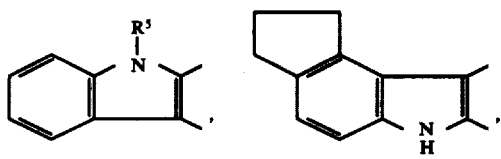

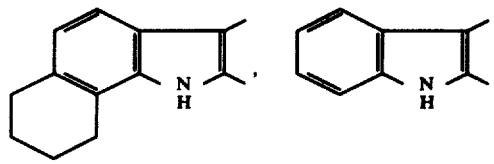

or 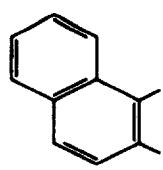

wherein $R^3$ and $R^4$ each are hydrogen, hydroxyl or lower alkoxy and $R^5$ is lower alkyl; $R^1$ is hydrogen, lower alkyl, phenyl or p-halophenyl; and $R^2$ is lower alkyl, amino(lower)alkyl, halo(lower)alkyl, $(CH_2)_n COOR^6$ wherein n is an integer from one to three and $R^6$ is lower alkyl, 2-furyl, 2-thienyl, 2-pyridyl, 3-pyridyl, 4-pyridyl, or

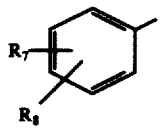

wherein $R^7$ and $R^8$ are the same or different and each represent hydrogen, halo, hydroxyl, carboxyl, carb(lower)alkoxy or phenyl; or $R^1$ and $R^2$ together with the carbon atom to which they are both joined form a radical of the formula

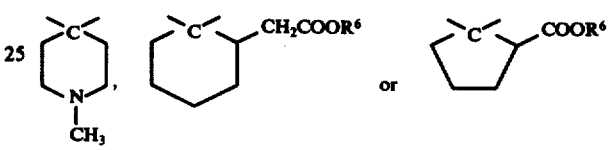

in which $R^6$ is lower alkyl; with the proviso that when A is

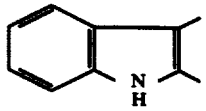

then $R^2$ is

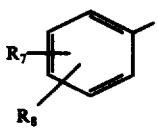

as defined herein, 2-furyl, 2-thienyl, 2-pyridyl, 3-pyridyl and 4-pyridyl, or $R^2$ and $R^1$ are joined in the manner described hereinbefore. These useful intermediates are prepared by a process which comprises treating a compound of formula II, B-Ch₂CH₂OH    II.

in which B is

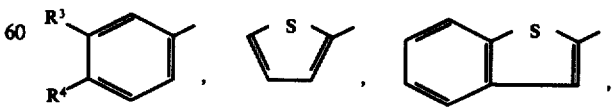

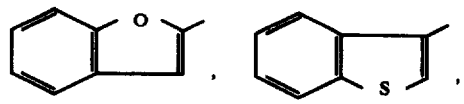

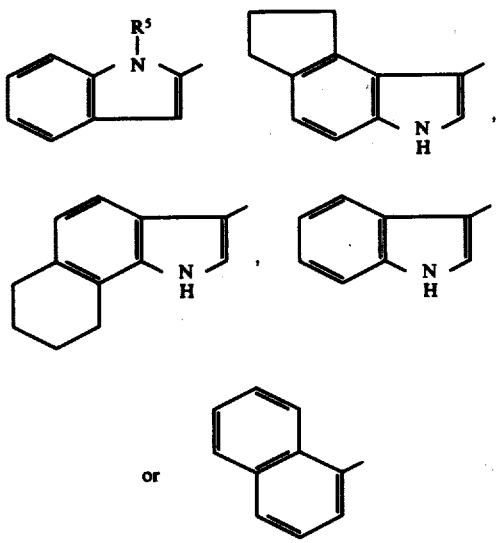

wherein $R^3$ and $R^4$ are as defined hereinbefore and $R^5$ is lower alkyl, with a compound of formula III,

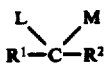    III.

in which $R^1$ and $R^2$ are as defined hereinbefore and L and M each represent lower alkoxy or together represent the ethylenedioxy radical or oxo, in the presence of an acid catalyst to obtain the respective, desired intermediate of formula I.

In the above two-dimensional representations of formula I and radical A, it is to be understood that the divalent radicals of formula A are joined to the remaining portion of formula I without inverting the two dimensional figures as shown.

DETAILED DESCRIPTION OF THE INVENTION

The term "lower alkyl" as used herein contemplates straight chain alkyl radicals containing from one to six carbon atoms and branched chain alkyl radicals containing three to four carbon atoms and includes methyl, ethyl, propyl, isopropyl, butyl, isobutyl, pentyl and the like.

The term "lower alkoxy" as used herein contemplates both straight and branched chain alkoxy radicals containing from one to four carbon atoms and includes methoxy, ethoxy, isopropoxy, t-butoxy and the like.

The term "halo" as used herein contemplates halogens and includes fluorine, chlorine, bromine and iodine.

The term "carb(lower)alkoxy" as used herein contemplates a carboxylic acid lower alkyl ester in which the alkyl portion thereof is coextensive with the aforementiond definition of lower alkyl.

PHARMACOLOGIC ACTIVITY

The ultimate products derived from the intermediates of formula I are exemplified by Examples 53 to 82. As noted herein they exhibit one or more of the following activities:

A. ANTIINFLAMMATORY AND ANALGESIC ACTIVITY

The useful antiinflammatory and analgesic activities of the ultimate products of this invention may be demonstrated in standard pharmacologic tests, for example, the tests described by R. A. Turner in "Screening Methods in Pharmacology," Academic Press, New York and London, 1965, pp. 152 – 163 and pp. 100 – 117, respectively.

More particularly, the antiinflammatory activity of the said ultimate products is demonstrated in a modification of the Freund's adjuvant test, the adjuvant induced acute edema test as described by J. R. Boissier, et al., Therapie, 25, 43 (1970). This test is known to correlate well with data derived from clinical results with humans. Boissier et al. have demonstrated this correlation with such clinically active compounds as phenylbutazone, mefenamic acid, indomethacin, aspirin, hydrocortisone and prednisolone.

More particularly exemplified, a substantial antiinflammatory effect for the compounds listed below is demonstrable at oral doses of 100 mg/kg/day in this actue edema test. In this test male rats are treated with the test compound one hour before the injection of Freund's adjuvant into the paw (day 0). The rats are then treated with the same dose of the test compund for the next three days. The anti-inflammatory effect of the test compound is measured by the reduction of pedal inflammation, see Turner cited above, and expressed as a percent inhibition from adjuvant injected control rats on day 3.

| Compound | Percent Inhibition |
|---|---|
| 1,2,3a,4,5,6-hexahydro-7,8-dimethoxy-pyrano[2,3,4-de]isoquinoline hydrochloride (Ex. 56) | 26% |
| N-methyl-1,2,3a,4,5,6-hexahydro-7,8-dimethoxypyrano[2,3,4-de]-isoquinoline hydrochloride (Ex. 57) | 14% |
| N,N-diethyl-6,7-dimethoxy-1-phenyl-1-isochromanpropylamine hydrochloride (Ex. 67) | 37% |
| 6,7-dihydro-4-methyl-4H-thieno[3,2-d]pyran-4-propionic acid (Ex. 69) | 27% |

When the said ultimate products derived from the intermediates of this invention are employed as antiinflammatory and analgetic agents in warm-blooded aniamls, e.g., rats, they may be administered orally, alone or in dosage forms, i.e., capsules or tablets, combined with pharmacologically acceptable excipients, such as starch, milk sugar and so forth. They may also be administered orally in the form of solutions in suitable vehicles such as vegetable oils.

The dosage of the said ultimate products will vary with the particular compound chosen and form of administration. Furthermore, it will vary with the particular host under treatment. Generally, the said products are administered at a concentration level that affords protective effects without any deleterious side effects. These antiinflammatorily-analgesically effective concentration levels are usually obtained within a therapeutic range of 1.0 mg to 500 mg/kg per day.

B. ANTIBACTERIAL AND ANTIFUNGAL ACTIVITY

Many of the ultimate products derived from the intermediates of this invention also exhibit utility as antibacterial agents against a number of gram-positive and gram-negative microorganisms, such as, Staphylococcus pyogenes, both penicillin sensitive and penicillin resistant, Streptococcus faecalis, Escherichia coil, Aerobacter aerogenes, Salmonella pullorum, Pseudomonas aerugenosa, Proteus mirabilis, Proteus vulgaris, Klebsiella pneumoniae and Serratia marcescens and as antifungal agents against a number of pathogenic fungi such as, Candida albicans, Microsporum gypseum and Trichophyton granulosum, in standard tests for antibacterial and antifungal activity, such as those described in "Antiseptics, Disinfectants, Fungicides and Sterilization," G. F. Reddish, Ed., 2nd ed., Lea and Febiger, Philadelphia, 1957 or by D. C. Grove and W. A. Randall in "Assay Methods of Antibiotics," Med. Encycl. Inc., New York 1955.

For Example, by employing a test like the serial broth dilution, see Grove and Randall, cited above, in which dilutions of the compounds of this invention in nutrient broth are inoculated with the microorganisms or fungi, described above, incubated at 37° C. for 2 days, respectively, and examined for the presence of growth, it may be shown that 1,2,3a,4,5,6-hexahydro-7,8-dimethoxypyrano[2,3,4-de]isoquinoline hydrochloride or 6,7-dimethoxy-N,N-dimethyl-1-1- 1-isochromanpropylamine hydrochloride is able to inhibit growth totally in this system of Proteus vulgaris, Klebsiella pneumoniae and Serratia marcescens at a concentration of 100 mcg/ml. or less.

When the said ultimate products are employed as antibiotic or antifungal agents in warm-blooded animals, e.g. rats, they may be administered alone or in combination with pharmacologically acceptable carriers. The proportion of the compound is determined by the solubility and chemical nature of the compound, chosen route of administration and standard biological practice. For example, they may be administered orally in solid form containing such excipients as starch, milk sugar, certain types of clay and so forth. The may also be administered orally in the form of solutions or they may be injected parenterally. For parenteral administration they may be used in the form of a sterile solution containing other solutes, for example, enough saline or glucose to make the solution isotonic.

The dosage of the present said ultimate products as antibiotic or antifungal agents will vary with the form of administration and the particular compound chosen. Furthermore, it will vary with the particular compounds chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford antibacterially or antifungally effective results without causing any harmful or deleterious side effects and preferably at a level that is in a range of fron about 1.0 mg. to about 1000 mg. per kilo per day, although as aforementioned variations will occur. However, a dosage level that is in the range of from about 10 mg. to about 500 mg. per kilo per day is most desirably employed in order to achieve effective results.

In addition, the said ultimate products may be employed topically. For topical application they may be formulated in the form of solutions, creams, or lotions in pharmaceutically acceptable vehicles containing 0.1-5 per cent, preferably 2 per cent, of the agent and may be administered topically to the infected area of the skin.

Also the antibacterial properties of the said ultimate products may be utilized for washing equipment in hospitals, homes and farms, instruments used in medicine and bacteriology, clothing used in bacteriological laboratories, and floors, walls and ceiling in rooms in which a background free of gram-positive and gram-negative microorganisms, such as those listed above, is desired. When employed in this manner the said ultimate products are formulated in a number of compositions comprising the active compound and an inert material. In such compositions, while the said ultimate products may be employed in concentrations as low as 500 p.p.m., from a practical point of view, it is desirable to use from about 0.10% by weight, to about 5% by weight or more.

The formulations that may be used to prepare antiseptic wash solutions of the compounds of this invention are varied and may readily be accomplished by standard techniques, see for example, "Remington's Practice of Pharmacy," E. W. Martin et al., Eds., 12th ed., Mack Publishing Company, Easton, Penn., 1961, pp 1121 – 1150. In general, the said ultimate products ae made up in stock solutions. They can also be formulated as suspensions in an aqueous vehicle. These make useful mixtures for decontaminating premises. Also, aqueous vehicles containing emulsifying agents, such as sodium lauryl sulfate, and relatively high concentrations, e.g., up to about 5% by weight, of the compounds may be formulated by conventional techniques.

A typical antiseptic preparation useful for disinfecting floors, walls, ceiling, and articles in a contaminated room may be prepared by adding 5 to 25 g. of 6,7-dimethoxy-N,N-dimethyl-1-phenyl-1-isochromanpropylamine hydrochloride to a mixture of 150 to 300 g. of polyethylene glycol 1540 and 150 to 300 g. of polyethylene glyol 300. The resulting mixture is stirred while a solution of 1 to 10 g. of sodium lauryl sulfate in 300 to 400 ml. of water is added portionwise. The article to be disinfected is coated or immersed in the preparation for a prolonged time, for example, one hour, and then rinsed with sterile water.

In practising the condensation (II + III → I) we have found it preferable to use a solvent as a reaction medium. Any solvent inert to the reaction conditions may be used. Suitable solvents include benzene, toluene, diethyl ether, dioxan, tetrahydrofuran, methylene dichloride, carbon tetrachloride and the like. Benzene and tetrahydrofuran are especially convenient and practical for this use. A variety of suitable acid catalysts may be used for this condensation, for example, the type of catalyst used in the Friedel Crafts reaction, i.e. p-toluenesulfonic acid, phosphorus pentoxide, boron trifluoride, zinc chloride, hydrochloric acid, sulfuric acid and the like. p-Toluenesulfonic acid, boron trifluoride, aluminum chloride and phosphorus pentoxide are included among the preferred acid catalysts. The amount of acid catalyst used is not especially critical and may range from 0.01 molar equivalents to 100 molar equivalents; however, a range of from 0.1 to 10 molar equivalents is generally preferred. The time of the reaction may range from 10 minutes to 60 hours, with the preferred range being from one-half to 24 hours. The temperature of the reaction may range from −20° C. to the boiling point of the reaction mixture. Preferred temperature ranges include 20° to 120° C.

Further details and exemplifications of practical and convenient conditions for the above condensation are found in our copending applications, Ser. Nos., 148,895 and 289,714, cited above.

The requisite starting materials of formula II of the present invention are either known or may be prepared by well known methods. For example, 3,4-dimethoxyphenethyl alcohol (IIa), 3-methoxyphenethyl alcohol (IIb) and 3-hydroxyphenethyl alcohol (IIc) have been described by E. Z. Khafagy and J. P. Lambooy, J. Med. Chem., 9, 936 (1966), 2-(2-thienyl)ethanol (IId) has been described by H. C. Van der Plas and C. J. Persoons, Rec. Trav. Chim., 83, 701 (1964), benzo[b]thiophene-2-ethanol (IIe) has been described by D. B. Capps and C. S. Hamilton, J. Amer. Chem. Soc., 75, 697 (1953) and benzo[b]thiophene-3-ethanol (IIf) has been described by E. Campaigne and E. S. Neiss, J. Heterocycl. Chem., 2, 231 (1965).

The starting materials of formula II, benzofuran-2-ethanol (IIg), nmr (CDCl$_3$) δ 2.33, 2.96, 3.88 and 6.40, and 2-(1-methylindole)ethanol (IIh), nmr (CDCl$_3$) δ 2.63 2.88, 3.55 and 6.12, are readily obtained by reacting benzofuran and N-methylindole, respectively, with ethylene oxide according to the method of M. Julia, et al., Bull. Soc. Chim. Fr., 2291 (1966) for preparing tryptophol.

The starting material of formula II, 1,4,5,6-tetrahydrocyclopent[e]indole-3-ethanol (IIi) is prepared by converting the amine, 5-indanamine, W. Borsche and G. John, Ber., 57, 656 (1924), to its corresponding diazonium chloride and reacting the latter compound with ethyl α-methyl acetoacetate in the presence of potassium hydroxide, followed by treatment of the resulting hydrazone with gaseous hydrochloric acid in ethanol according to the conditions of the Japp-Klingemann and Fischer Indole reactions (see for example, P. L. Julian, et al., "Heterocyclic Compounds", R. C. Elderfield, Ed., Vol. 3, John Wiley and Sons, Inc., New York, 1952, p.p. 11 – 13 to give 1,4,5,6-tetrahydrocyclopent[e]indole-2-carboxylic acid ethyl ester. The latter compound is hydrolyzed with methanolic aqueous potassium hydroxide, followed by decarboxylation in quinoline (230° C.) to give 1,4,5,6-tetrahydrocyclopent[e]indole. The latter indole derivative is readily converted to the above starting material of compound II by known procedures; for example, see T. Nogrady and T. W. Doyle, Can. J. Chem., 42, 485 (1964). More specifically this conversion involves treating the said latter indole derivative with oxalyl chloride and then ethanol to afford the corresponding glyoxylate derivative which on treatment with lithium aluminum hydride affords the desired starting material of formula II.

Finally, the requisite starting materials of formula III are either well known or prepared by known laboratory methods. For example, a comprehensive review on the properties and preparation of β, γ and δ-ketoacids and -ketoesters may be found in "Rodd's Chemistry of the Carbon Compounds, " cited above, Vol. 1d, pp. 226–274. Likewise, the ketones used herein are either available commercially, for example, acetone or γ-chlorobutyrophenone, or they are prepared by conventional methods; for example, see P. Karrer, "Organic Chemistry, "]2nd. ed., Elsevier Publishing Co., Inc., New York, 1946, p.p. 149 – 169 and V. Migrdichian, "Organic Synthesis, " Vol. 1, Reinhold Publishing Corp., New York, 1957. pp. 100 – 129.

The following examples illustrate further this invention.

EXAMPLE 1

6,7-Dimethoxy-1-isochromanmethylamine

A solution of the starting material of formula II, 3,4-dimethoxyphenethyl alcohol (108 g), described by E. Z. Khafagy and J. P. Lambooy, J. Med. Chem., 9, 936 (1966), and the starting material of formula III, aminoacetaldehyde diethyl acetal (78 g), in dry dioxane (250 ml) is stirred and cooled (ice bath) while being saturated with hydrogen chloride over a period of one hour. The mixture is kept at room temperature for two days. The crystalline precipitate is collected, washed with dry dioxane and then ether to yield the hydrochloric acid addition salt (hydrochloride) of the title compound, m.p. 250°–255° C. (dec.), after recrystallization from methanol.

This hydrochloric acid addition salt exhibits antibacterial activity.

The title compound (free base), obtained by shaking a chloroform solution of the above hydrochloric acid addition salt with 5% sodium hydroxide solution, followed by concentration of the chloroform solution, has $\lambda_{max}^{EtOH}$ 285 nm (3650), 281 nm (7580); nmr (CDCl$_3$) δ 3.92, 5.14.

In the same manner but replacing the addition of hydrogen chloride with an initial addition of 12.0 g. of p-toluenesulfonic acid, boron trifluoride etherate, phosphorus pentoxide or aluminum chloride, the title compound is also obtained.

In the same manner but replacing 3,4-dimethoxyphenethyl alcohol and aminoacetaldehyde diethyl acetal with equivalent amounts of phenethyl alcohol, Khafagy and Lambooy, cited above, and ethyl acetoacetate, respectively, 1-methyl-1-isochromanacetic acid ethyl ester, $\nu_{max}^{CHCl_3}$ 1720 cm$^{-1}$, nmr (CDCl$_3$) δ 1.5, 2.85, is obtained. Likewise, replacement with equivalent amounts of 1-naphthaleneethanol, M. Mousseron and Nguyen-Phuoc-Du. Bull. Soc. Chim. Fr., 91 (1948), and ethyl acetoacetate, gives 1,2-dihydro-4-methyl-4H-naphtho [2,1-c]pyran-4-acetic acid ethyl ester, $\nu_{max}^{CHCl_3}$ 1720 cm$^{-1}$, nmr (CDCl$_3$) δ1.5. Hydrogen bromide is a preferred acid catalyst for these latter two preparations.

By following the procedure of Example 1 but using the appropriate starting materials of formulae II and III as listed in Examples 2 to 52, then the corresponding compounds of formula I, the products of Examples 2 to 52, are also obtained.

In these examples the designation superscript[1] following the name of the product indicates that it exhibits antiinflammatory activity, the designation superscript[3] indicates antibacterial activity and the designation superscript[3] indicates antifungal activity.

STARTING MATERIAL OF
FORMULA III

-continued

| EX. | STARTING MATERIAL OF FORMULA II | L\C/M | R¹ | R² | PRODUCT: |
|---|---|---|---|---|---|
| 2 | 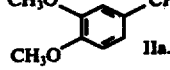 CH₃O—⟨ ⟩—CH₂CH₂OH, CH₃O   IIa. | EtO\C/OEt | H | CH₂Br | 6,7-dimethoxy-1-iso-chromanmethyl bromide, m.p. 78–80° C. |
| 3 | " | C=O | H | CH₂CH₂Cl | 6,7-dimethoxy-1-iso-chromanethyl chloride, nmr (CDCl₃) δ 3.86, 4.98 |
| 4 | " | C=O | H |  Cl—⟨phenyl⟩— | 1-(4-chlorophenyl)-6,7-dimethoxyiso-chroman, m.p. 81–83° C.[3] |
| 5 | " | C=O | H | 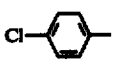 COOH—⟨phenyl⟩— | p-(6,7-dimethoxy-1-isochromanyl)benzoic acid, m.p. 140–143° C.[2] |
| 6 | " | C=O | H | 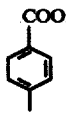 2,6-diCl-phenyl | 1-(2,6-dichloro-phenyl)-6,7-dimethoxy-isochroman, m.p. 95–98° C.[2,3] |
| 7 | " | C=O | H | 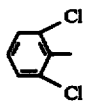 OH—⟨phenyl⟩— | m-(6,7-dimethoxyiso-chroman-1-yl)phenol, m.p. 135–137° C.[2,3] |
| 8 | " | C=O | H | 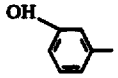 2-furyl | 1-(2-furyl)-6,7-di-methoxyisochroman, m.p. 94–96° C.[1,2] |
| 9 | " | C=O | H |  2-thienyl | 6,7-dimethoxy-1-(2-thienyl)isochro-man, m.p. 78–81° C.[2,3] |
| 10 | " | C=O | H |  3-pyridyl | 6,7-dimethoxy-1-(3-pyridyl)isochro-man, nmr (CDCl₃) δ 3.79, 3.94, 6.17, corresponding oxalic acid addition salt has m.p. 143–145° C.[1,3] |
| 11 | " | C=O | H | 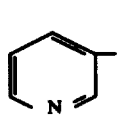 2-pyridyl | 6,7-dimethoxy-1-(2-pyridyl)isochro-man, nmr (CDCl₃) δ 3.65, 3.82, 6.14, corresponding oxalic acid addition salt has m.p. 136–139° C.[3] |
| 12 | " | C=O | CH₃ | 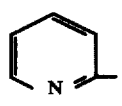 4-pyridyl | 4-(6,7-dimethoxy-1-methylisochroman-1-yl)-pyridine, nmr (CDCl₃) δ 1.95, 3.87, 3.90, corresponding hydro-chloric acid addition salt has m.p. 208–211° C.[3] |
| 13 | " | C=O | 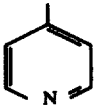 phenyl | (CH₂)₃Cl | 6,7-dimethoxy-1-phenyl-1-isochromanpropyl chloride, m.p. 125–126° C. |
| 14 | " | C=O |  4-fluorophenyl | (CH₂)₃Cl | 6,7-dimethoxy-1-(4-fluorophenyl)-1-isochromanpropyl chloride, m.p. 90–93° C.[2] |
| 15 | " | C=O | CH₃ | CH₂COOC₂H₅ | 6,7-dimethoxy-1-methyl-1-isochroman-acetic acid ethyl ester, λ$_{max}^{EtOH}$ 284 nm (3390), 281 nm (6840) |
| 16 | " | C=O | CH₃ | (CH₂)₂COOH | 6,7-dimethoxy-1-methyl-1-isochroman-propionic acid, λ$_{max}^{EtOH}$ 284 nm (3120), 280 nm (5840)[1] |

| | | | | | |
|---|---|---|---|---|---|
| 17 | " | C = O | CH₃ |  | 6,7-dimethoxy-1-methyl-1-phenylisochroman, m.p. 93 – 95° C. |
| 18 | " | C = O | CH₃ | 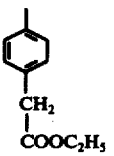 | [p-(6,7-dimethoxy)-1-methylisochroman-1-yl)phenyl]acetic acid ethyl ester, m.p. 70 – 72° C. |
| 19 | " | C = O | CH₃ | 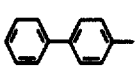 | 1-(4-biphenylyl)-6,7-dimethoxy-1-methylisochroman, m.p. 94 – 96° C. |
| 20 | 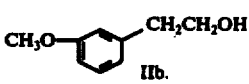 IIb. | OEt C OEt | H | CH₂NH₂ | 6-methoxy-1-isochromanmethylamine, nmr (CDCl₃) δ 3.84, 5.11, corresponding hydrochloric acid addition salt has m.p. 166–168° C.² |
| 21 | 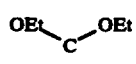 IIc. | C = O | H | 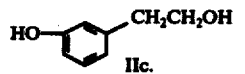 | 1-(2-thienyl)-6-isochromanol, m.p. 126–120° C.³ |
| 22 | " | C = O | CH₃ | 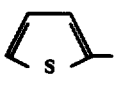 | 1-methyl-1-(3-pyridyl)-6-isochromanol, m.p. 178 – 180° C. |
| 23 | 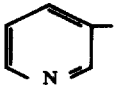 IId. | OEt C OEt | H | CH₂NH₂ | 6,7-dihydro-4H-thieno-[3,2-c]pyran-4-methylamine, δ $_{max}^{EtOH}$ 233 nm (6370), corresponding hydrochloric acid has m.p. 204 – 206° C.³ |
| 24 | " | OEt C OEt | H | CH₂CH₂Cl | 6,7-dihydro-4H-thieno-[3,2-c]pyran-4-ethylchloride, nmr(CDCl₃) δ 3.70, 6.73, 7.09 |
| 25 | " | C = O | CH₃ | CH₂COOC₂H₅ | 6,7-dihydro-4-methyl-4H-thieno[3,2-d]-pyran-4-acetic acid ethyl ester, ν $_{max}^{CHCl_3}$ 1732 cm⁻¹ |
| 26 | " | C = O | CH₃ | (CH₂)₂COOCH₃ | 6,7-dihydro-4-methyl-4H-thieno[3,2-c]pyran-4-propionic acid methyl ester ν $_{max}^{CHCl_3}$ 1735 cm⁻¹ |
| 27 | " | C = O | H |  | 4-(6,7-dihydro-4H-thieno[3,2-c]pyran-1-yl)pyridine, m.p. 99–101° C, corresponding hydrochloric acid addition salt has m.p. 212 – 215° C.² |
| 28 | " | C = O | H | 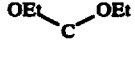 | 3-(6,7-dihydro-4H-thieno[3,2-c]pyran-4-yl)pyridine, nmr (CDCl₃) δ 2.97, 6.47, 7.09, corresponding oxalic acid addition salt has m.p. 132–134° C.² |
| 29 | " | C = O | CH₃ | CH₃ | 4,4-dimethyl-6,7-dihydro-4H-thieno-[3,2-c]pyran, b.p. 60° C/0.1mm. |
| 30 | 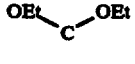 IIe. | OEt C OEt | H | CH₂CH₂Cl | 3,4-dihydro-1H-[1]-benzothieno[3,2-c]-pyran-1-ethylchloride m.p. 92 – 94° C. |
| 31 | " | C = O | CH₃ | CH₂COOEt | 3,4-dihydro-1-methyl- |

-continued

| | | | | | |
|---|---|---|---|---|---|
| | | | | | 1H-[1]benzothieno-[3,2-c]pyran-1-acetic acid ethyl ester, $\delta_{max}^{CHCl_3}$ 1731 cm$^{-1}$ |
| 32 | " | C=O | H | 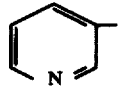 | 3-(3,4-dihydro-1H-[1]benzothieno-[3,2-c]pyran-1-yl)-pyridine, nmr(CDCl$_3$) $\delta$ 2.87, 5.97, corresponding hydrochloric acid addition salt has m.p. 217 – 220° C.$^2$ |
| 33 | 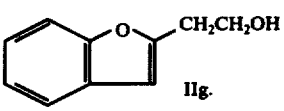 IIg. | C=O | CH$_3$ | CH$_2$COOC$_2$H$_5$ | 3,4-dihydro-1-methyl-1H-pyrano[4,3-b]-benzofuran-1-acetic acid ethyl ester, $\nu_{max}^{CHCl_3}$ 1734 cm$^{-1}$ |
| 34 | 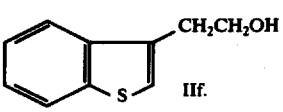 IIf. | OEt\_C\_OEt | H | CH$_2$NH$_2$ | 3,4-dihydro-1H-[1]-benzothieno[2,3-c]-pyran-1-methylamine, nmr (CDCl$_3$) $\delta$ 2.87, 4.00, 5.92, corresponding maleic acid addition salt has m.p. 169–171° C. |
| 35 | " | OEt\_C\_OEt | H | CH$_2$CH$_2$Cl | 3,4-dihydro-1H-[1]-benzothieno[2,3-c]-pyran-1-ethyl chloride, nmr (CDCl$_3$) $\delta$ 2.84, 5.02 |
| 36 | " | 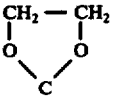 | CH$_3$ | (CH$_2$)$_3$Cl | 3,4-dihydro-1-methyl-1H-[1]benzothieno[2,3-c]-pyran-1-propyl chloride nmr (CDCl$_3$) $\delta$ 2.80, 4.60 |
| 37 | " | C=O |  | (CH$_2$)$_3$Cl | 3,4-dihydro-1-phenyl-1H-[1]-benzothieno[2,3-c]-pyran-1-propyl chloride nmr (CDCl$_3$) $\delta$ 1.87, 3.30 |
| 38 | " | C=O | CH$_3$ | CH$_2$COOC$_2$H$_5$ | 3,4-dihydro-1-methyl-1H-benzothieno[2,3-c]pyran-1-acetic acid ethyl ester, $\nu_{max}^{CHCl_3}$ 1732 cm$^{-1}$ |
| 39 | " | C=O | CH$_3$ | 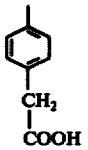 | [p-(3,4-dihydro-1-methyl-1H-[1]benzothieno[2,3-c]pyran-1-yl)phenyl]-acetic acid, m.p. 120 – 122° C. |
| 40 | " | C=O | H | 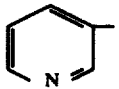 | 3-(3,4-dihydro-1H-[1]-benzothieno[2,3-c]-pyran-1-yl)pyridine, m.p. 119 – 121° C. |
| 41 | 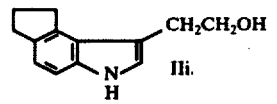 IIi. | C=O | n-C$_3$H$_7$ | CH$_2$COOC$_2$H$_5$ | 2,3,6,7,9,10-hexahydro-7-propyl-1H-cyclopenta-[e]pyrano[3,4-b]indole-7-acetic acid ethyl ester, $\nu_{max}^{CHCl_3}$ 3410, 1709 cm$^{-1}$ |
| 42 | 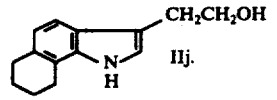 IIj. | C=O | CH$_3$ | CH$_2$COOC$_2$H$_5$ | 1,2,3,4,7,8,10,11-octahydro-10-methylbenzo-[g]pyrano[3,4-b]indole-10-acetic acid ethyl ester, $\nu_{max}^{CHCl_3}$ 3410, 1714 cm$^{-1}$ |
| 43 | " | C=O | n-C$_3$H$_7$ | CH$_2$COOC$_2$H$_5$ | 1,2,3,4,7,8,10,11-octahydro-10-propylbenzo-[g]pyrano[3,4-b]indole-acetic acid ethyl ester $\nu_{max}^{CHCl_3}$ 1710 cm$^{-1}$ |

-continued

| EX. | STARTING MATERIAL OF FORMULA II | | | PRODUCT: |
|---|---|---|---|---|
| 44 | indole with N-CH₃ and 2-CH₂CH₂OH substituent (IIh) | C=O | CH₃ | CH₂COOC₂H₅ | 1,5-dimethyl-1,3,4,5-tetrahydropyrano-[4,3-b]indole-1-acetic acid ethyl ester, $\nu_{max}^{CHCl_3}$ 1732 cm$^{-1}$. |

| EX. | STARTING MATERIAL OF FORMULA II | STARTING MATERIAL OF FORMULA III | PRODUCT: |
|---|---|---|---|
| 45 | 3,4-dimethoxyphenyl-CH₂CH₂OH | 1-methyl-4-piperidone | 6,7-dimethoxy-1-methyl-spiro[isochroman-1,4'-piperidine], $\lambda_{max}^{EtOH}$ 284 nm (3830), 280 nm (3780), 228 nm (8200), corresponding hydrochloric acid addition salt has m.p. 234–236° C.[1,2] |
| 46 | 3-methoxyphenyl-CH₂CH₂OH | 1-methyl-4-piperidone | 6-methoxy-1'-methyl-spiro[isochroman-1,4'-piperidine], $\lambda_{max}^{EtOH}$ 284 nm (3830), 280 nm (3780), 228 nm (8200), nmr (CDCl₃) δ 2.82, 3.72 corresponding hydrochloric acid addition salt has m.p. 245–248° C.[2] |
| 47 | 3-hydroxyphenyl-CH₂CH₂OH | 1-methyl-4-piperidone | 1'-methylspiro[isochroman]-1,4'-piperidin]-6-ol, $\lambda_{max}^{EtOH}$ 281 nm (3920), 274 nm (3800), corresponding hydrochloric acid addition salt has m.p. >270° C.[2] |
| 48 | thiophene-2-CH₂CH₂OH | 1-methyl-4-piperidone | 4,5-dihydro-1-methyl-spiro[piperidine-4,7'-[7H]thieno[2,3-c]pyran] $\lambda_{max}^{EtOH}$ 234 nm (6940), corresponding hydrochloric acid addition salt has m.p. 220–222° C.[1,2] |
| 49 | benzothiophene-CH₂CH₂OH | 1-methyl-4-piperidone | 3,4-dihydro-1'-methyl-spiro[1H-[1]-benzothieno[3,2-c]pyran-1,4'-piperidine], nmr(CDCl₃) 2.89, 3.99, corresponding hydrochloric acid addition salt has m.p. >270° C.[1] |
| 50 | indole-3-CH₂CH₂OH (NH) | ethyl 2-cyclohexanone acetate | 4',9'-dihydrospiro-[cyclohexane-1,1'(3'H)-pyrano[3,4-b]indole]-2-acetic acid ethyl ester, m.p. 131–135° C. |
| 51 | indole-3-CH₂CH₂OH (NH) | ethyl 2-cyclopentanone carboxylate | 4',9'-dihydrospiro-cyclopentane-1,1'(3'H)-pyrano[3,4-b]indole]-2-carboxylic acid ethyl ester, $\nu_{max}^{CHCl_3}$ 1734 cm$^{-1}$ |
| 52 | indole-3-CH₂CH₂OH (NH) | 1-acetyl-4-piperidone | 1-acetyl-4',9'-dihydrospiro[piperidine-4,1'-(3'H)-pyrano[3,4-b]-indole], m.p. 300–305° C. |

EXAMPLE 53

6,7-Dimethoxy-N-methyl-1-isochromanmethylamine

A mixture of 6,7-dimethoxy-1-isochromanmethylamine hydrochloride (6.0 g), described in Example 1, and 37% formaldehyde solution (12 ml) is heated on the steam bath under a reflux condenser for 20 min. A further 6 ml formaldehyde solution is added and heating is continued for 20 min. The solution is evaporated to dryness and the residue is crystallized from isopropanol to give the hydrochloric acid addition salt of the title compound, m.p. 254°–256° C. (dec.).

The title compound (free base), obtained from the hydrochloric acid addition salt in the usual manner, for instance see Example 1, has $\lambda_{max}^{EtOH}$ 281 nm (3700) and 285 nm (230).

The hydrochloric acid addition salt exhibits antibacterial activity.

EXAMPLE 54

N,N-Dimethyl-6,7-dimethoxy-1-isochromanmethylamine

A mixture of 6,7-dimethoxy-1-isochromanmethylamine (7.5 g), formic acid (35 ml) and 37% formaldehyde solution (35 ml) is heated on the steam bath for 3 hr. the mixture is concentrated to a small volume under reduced pressure and the residue is diluted with 2N NaOH solution and extracted with chloroform. The extracts are washed with brine, dried (MgSO$_4$) and evaporated to leave the title compound, $\lambda_{max}^{EtOH}$ 284 nm (3460) and 230 nm (7390).

The corresponding hydrochloric acid addition salt of the title compound has m.p. 189°–192° C.

The hydrochloride acid addition salt exhibits antibacterial and antiinflammatory activities.

EXAMPLE 55

N-Benzyl-6,7-dimethoxy-1-isochromanmethylamine

A mixture of 6,7-dimethoxy-1-isochromanmethylamine (18.0 g), benzaldehyde (9.7 g) and dry benzene (400 ml) is heated under reflux (Dean-Stark) for 18 hr. The solvent is removed under reduced pressure and the residue (27.0 g) is dissolved in ethanol (400 ml). Sodium borohydride (17.0 g) is added portionwise to the stirred solution. When the addition is complete the mixture is stirred and heated under reflux for 1.5 hr. and then left at room temperature overnight. The mixture is concentrated, diluted with water and extracted with ether. The ether extracts are in turn extracted with 10% HCl and these extracts are made alkaline and re-extracted with ether. These extracts are washed with brine, dried and evaporated to give the title compound, $\lambda_{max}^{EtOH}$ 285 nm (3750) and 281 nm (4000).

The corresponding hydrochloric acid addition salt has m.p. 163°–165° C. and exhibits antibacterial activity.

EXAMPLE 56

1,2,3a, 4,5,6-Hexahydro-7,8-dimethoxypyrano[2,3,4-de]-isoquinoline

Formaldehyde solution (50 ml of 37%) is added to a solution of 6,7-dimethoxy-1-isochromanmethylamine (45.5 g), described in Example 1, in methanol (150 ml). The mixture is kept at room temperature for 2 hr. (All the starting material had been consumed judging by TLC).

Most of the methanol is removed under reduced pressure keeping the temperature below 45° C. The residue is dissolved in chloroform and this solution is evaporated (temp. 45°). The residue is dissolved in dry dioxane (300 ml) and this solution is dried for 1 hr. over molecular sieves. The sieves are removed and the solution is stirred and saturated with HCl gas (1 hr) at ice bath temperature and then kept at room temperature overnight and then evaporated to dryness. The residue is re-evaporated several times with isopropanol and then crystallized from methanol to give the hydrochloric acid addition salt of the title compound, m.p. 235°–238° C.

The title compound (free base), obtained from the hydrochloride addition salt in the usual manner, for instance see Example 1, has $\lambda_{max}^{EtOH}$ 285 nm (2420).

The hydrochloric acid addition salt exhibits antibacterial and antiinflammatory activities.

EXAMPLE 57

N-Methyl-1,2,3a, 4,5,6-hexahydro-7,8-dimethoxypyrano[2,3,4-de]-isoquinoline

A mixture of 1,2,3a,4,5,6-hexahydro-7,8-dimethoxypyrano[2,3,4-de]isoquinoline hydrochloride (7.0 g), described in Example 56, 37% formaldehyde solution (35 ml) and formic acid (35 ml) is heated on the steam bath for 3 hr. The mixture is evaporated, diluted with water, made alkaline and extracted with chloroform. The extracts were washed with brine, dried, evaporated to give the title compound, $\lambda_{max}^{EtOH}$ 285 nm (2410).

The corresponding hydrochloric acid addition salt of the title compound has m.p. 210°–214° C., after recrystallization from isopropanol. This salt exhibits antibacterial and antiinflammatory activities.

EXAMPLE 58

5-Acetyl-1,2,3a,4,5,6-hexahydro-7,8-dimethoxypyrano[2,3,4-de]isoquinoline

A mixture of 1,2,3a, 4,5,6-hexahydro-7,8-dimethoxypyrano[2,3,4-de]isoquinoline (10.0 g), described in Example 56, acetic anhydride (60.0 ml) and pyridine (0.5 ml) is heated on the steam bath for 4 hr. The mixture is poured into water and stirred for 2 hr. The mixture is extracted with chloroform and the extracts are washed with sodium bicarbonate solution and then with brine. The organic solution is dried and evaporated to leave the title compound. A sample, crystallized from isopropanol, had m.p. 100°–102° C.

The title compound exhibits antibacterial activity and is useful for the preparation of the following compound.

EXAMPLE 59

5-Ethyl-1,2,3a,4,5,6-hexahydro-7,8-dimethoxypyrano[2,3,4-de]isoquinoline

A solution of the N-acetyl compound, 5-acetyl-1,2,3a,4,5,6-hexahydro-7,8-dimethoxy[2,3,4-de]-isoquinoline (9.0 g), described in Example 58, in anhydrous tetrahydrofuran (100 ml) is added dropwise to a stirred suspension of lithium aluminium hydride (5.0 g) in tetrahydrofuran (50 ml). The mixture is then heated under reflux for 3 hr. The excess hydride is destroyed with a mixture of water (30 ml) and tetrahydrofuran (80 ml). The suspension is filtered and the filtrate evaporated. The residue is dissolved in chloroform and washed with water. The organic solution is dried and evaporated to yield the title compound, nmr (CDCl$_3$) δ 2.87, 4.00.

The corresponding hydrochloric acid addition salt the title compound has m.p. 207°–210° C. and has antibacterial and antifungal activity.

EXAMPLE 60

1,2,3a,4,5,6-Hexahydro-7,8-dimethoxypyrano[2,3,4-de]-isoquinoline-5-carboxamide A solution of sodium cyanate (2.0 g) in water (20 ml) is added dropwise to a solution of 1,2,3a,4,5,6-hexahydro-7,8-dimethoxypyrano[2,3,4-de]isoquiniline (2.0 g), described in Example 56, (2.0 g) in acetic acid (8.0 ml) and water (12.0 ml). the mixture is left at room temperature for 6 hr. and the precipitate is then collected, washed with water, and crystallized from methanol to give the title compound, m.p. 224°–226° C.

The title compound has antibacterial activity.

EXAMPLE 61

5-Cyanoethyl-1,2,3a,4,5,6-hexahydro-7,8-dimethoxypyrano[2,3,4-de]isoquinoline

A solution of acrylonitrile (12 ml) and 1,2,3a,4,5,6-hexahydro-7,8-dimethoxypyrano[2,3,4-de]isoquinoline (11 g), described in Example 56, in dioxane (80 ml) and 10% NaOH solution (2.5 ml) is heated and stirred on the steam bath for 24 hr. The mixture is evaporated and the residue is dissolved in a mixture of ether and a little chloroform. The solution is extracted with 2N HCl and the extracts are washed (brine), dried and evaporated. The residue is crystallized from ether and then from benzene-hexane to give the title compound, m.p. 105°–107° C.

The title compound is used for the preparation of the following compound.

EXAMPLE 62

5-(3-Aminopropyl)-1,2,3a,4,5,6-hexahydro-7,8-dimethoxypyrano[2,3,4-de]isoquinoline dihydrochloride A solution of aluminum chloride (5.6 g) in anhydrous ether (80 ml) is added dropwise to a stirred suspension of lithium aluminum hydride (1.6 g) in anhydrous ether (80 ml). The mixture is stirred at room temperature for 0.5 hr. and then a solution of the nitrile, 5-cyanoethyl-1,2,3a,4,5,6-hexahydro-7,8-dimethoxypyrano[2,3,4-de]-isoquinoline (7 g), described in Example 61, in anhydrous ether (100 ml) is added dropwise during 2 hr. The mixture is heated under reflux for 2 hr. and then cooled (ice bath) and a solution of water (12 ml) in tetrahydrofuran (60 ml) is added. The mixture is heated under reflux for 15 minutes, cooled and water (20 ml) is added, followed by 10% KOH solution until the aqueous phase is rendered basic. The mixture is filtered, washing well with ether. The ether solution is collected and the aqueous phase is saturated with salt and extracted with chloroform. The organic solutions are combined and evaporated to yield the title compound, $\lambda_{max}^{EtOH}$ 284 nm (1830).

The corresponding hydrochloric acid addition salt has m.p. 168°–172° C., after recrystallization from isopropanol.

The title compound is useful for the preparation of the following compound.

EXAMPLE 63

5-[3-(Dimethylamino)propyl]-1,2,3a,4,5,6-hexahydro-7,8-dimethoxypyrano[2,3,4-de]isoquinoline By following the procedure of Example 2 but replacing 6,7-dimethoxy-1-isochromanmethylamine with an equivalent amount of 5-(3-aminopropyl)-1,2,3a,4,5,6-hexahydro-7,8-dimethoxypyrano[2,3,4-de]isoquinoline, described in Example 62, the title compound, nmr (CDCl$_3$) δ 2.24, 3.81, 3.84, 4.62, 6.57, is obtained.

The corresponding hydrochloric acid addition salt has m.p. 205°–207° C., after crystallization from isopropanol.

The hydrochloric acid addition salt exhibits antibacterial activity.

EXAMPLE 64

6,7-Dimethoxy-N,N-dimethyl-1-isochromanethylamine

A mixture of 6,7-dimethoxy-1-isochromanethyl chloride (6.0 g), described in Example 3, 25% aqueous dimethylamine (90 ml) and dioxane (30 ml) is stirred at room temperature for 18 hr. and then heated on the steam bath for 3 hr. The mixture is concentrated and extracted with chloroform. The extracts are washed with brine, dried, and evaporated to yield the title compound, $\lambda_{max}^{EtOH}$ 229 nm (7500), 281 nm (3710) and 284 nm (3720).

The hydrochloric acid addition salt of the title compound has m.p. 163°–166° C.

In the same manner but replacing the dimethylamine with an equivalent amount of N-methylpiperazine, 1-[2-(6,7-dimethoxyisochroman-1-yl)ethyl]-4-methylpiperazine, $\lambda_{max}^{EtOH}$, 224 nm (7000), 228 nm (7030), 282 nm (3330), is obtained; the corresponding oxalic acid addition salt (dioxalate) thereof having m.p. 239°–242° C., after recrystallization from methanol.

In the same manner but replacing the dimethylamine with an equivalent amount of diethylamine, N,N-diethyl-6,7-dimethoxy-1-isochromanethylamine, $\lambda_{max}^{EtOH}$ 224 nm (3600) and 282 nm (3530), is obtained; the corresponding oxalic acid addition salt thereof having m.p. 120°–122° C., after crystallization from isopropanol-ether.

The three hydrochloric acid addition salts of this example exhibit antibacterial and antiinflammatory activities.

EXAMPLE 65

N-Carbethoxy-3,4-dihydro-6,7-dimethoxyspiro(isochroman-1,4'-piperidine)

A solution of 6,7-dimethoxy-1'-methylspiro[isochroman-1,4'-piperidine] (9.4 g), described in Example 45, in dry benzene (35 ml) is added dropwise to a stirred boiling solution by ethyl chloroformate (7.5 g) in dry benzene (30 ml). The mixture is heated at reflux for 4 hrs., left overnight at room temperature, a further portion (3.25 g) of ethyl chloroformate added, and the mixture is heated at reflux for a further 6 hr. The mixture is evaporated to dryness and the residue chromatographed (alumina 111 neutral). Elution with benzene gives the title compound $\lambda_{max}^{EtOH}$ 284 nm (3450), 280 nm (7910).

This compound is used to prepare the following secondary amine.

EXAMPLE 66

6,7-Dimethoxyspiro(isochroman-1,4'-piperidine)

A mixture of N-carbethoxy-3,4-dihydro-6,7-dimethoxyspiro(isochroman-1,4'-piperidine) (10.0 g), described in Example 65, in 100 ml of ethanol and 100 ml of 50% aqueous sodium hydroxide is heated at reflux for 2.5 hr. The mixture is concentrated, diluted with water and extracted with chloroform. The extracts are washed (brine), dried and evaporated to yield the title compound, nmr (CDCl$_3$) δ 2.80, 3.99.

The corresonding hydrochloric acid addition salt m.p. 213–°215° and exhibits antibacterial activity.

EXAMPLE 67

6,7-Dimethoxy-N,N-dimethyl-1-phenyl-1-isochromanpropylamine

A mixture of 6,7-dimethoxy-1-phenyl-1-isochromanpropyl chloride (10.0 g), described in Example 13, 40% aqueous dimethylamine (60 ml) and dioxane (50 ml) is heated under reflux for 18 hr. The mixture is concentrated, made alkaline and extracted with chloroform. The chloroform extracts are dried and evaporated to yield the title compound, $\lambda_{max}^{EtOH}$ 282 nm (4070), 285 nm (4250).

The corresponding hydrochloric acid addition salt of the title compound has m.p. 211°–213° C. after crystallization from isopropanol. This salt exhibits antibacterial activity.

In the same manner but replacing the dimethylamine with an equivalent amount of N-methylpiperazine, 1-[3-(6,7-dimethoxy-1-phenylisochroman-1-yl)propyl]-4-methylpiperazine, nmr (CDCl$_3$) δ 3.40, 7.00, 7.45, is obtained; the corresponding hydrochloric acid addition salt (dihydrochloride) thereof having m.p. 243.5°–244.5° C., after crystallization from isopropanol. This salt exhibits antibacteral activity.

In the same manner but replacing the dimethylamine with an equivalent amount of diethylamine, N,N-diethyl-6,7-dimethoxy-1-phenyl-1-isochromanpropylamine, $\lambda_{max}^{EtOH}$ 286 nm (3670) and 283 nm (4560), is obtained; the corresponding hydrochloric acid addition salt having m.p. 192°–194° C. after crystallization from isopropanol. This salt exhibits antiinflammatory and antibacterial activity.

EXAMPLE 68

6,7-Dimethoxy-N,N-dimethyl-1-(4-fluorophenyl)-1-isochromanpropylamine

A mixture of 6,7-dimethoxy-1-(4-fluorophenyl)-1-isochromanpropyl chloride (8.0 g), described in Example 14, 40% aqueous dimethylamine (150 ml) and dioxane (150 ml) is stirred at room temperature for 48 hr. The mixture is concentrated, rendered alkaline and extracted with chloroform. The chloroform extracts are dried (MgSO$_4$) and concentrated to yield the title compound, $\lambda_{max}^{EtOH}$ 286 nm (3920) and 282 nm (4170).

The corresponding hydrochloric acid addition salt of the title compound has m.p. 205° C. after recrystallization from isopropanol-ether and exhibits antibacterial activity.

In the same manner but replacing dimethylamine with an equivalent amount of pyrrolidine, 1-{3-[1-(4-fluorophenyl)-6,7-dimethoxy-1-isochromanyl]propyl}pyrrolidine, $\lambda_{max}^{EtOH}$ 286 nm (3,990), 282 nm (4010), is obtained, the corresponding hydrochloric acid addition salt thereof having m.p. 202°–204° C., after crystallization from isopropanol-ether. This latter salt exhibits antibacterial activity.

EXAMPLE 69

6,7-Dimethoxy-1-methylisochromanacetic acid

A solution of the corresponding ethyl ester of the title compound (28.0 g), described in Example 15, in ethanol (500 ml) is treated with 10% sodium hydroxide solution (250 ml) and kept overnight at room temperature. The solution is then concentrated under reduced pressure to ½ volume, washed with ether and rendered acid with conc. HCl. The mixture is extracted with ether. The extracts are washed with brine, dried and evaporated and the residue is crystallized from benzene-hexane to give the title compound, m.p. 89°–92° C.

The title compound exhibits antifungal activity and antiinflammatory activity.

In the same manner but replacing the above corresponding ethyl ester with an equivalent amount of [p-(6,7-dimethoxy-1-methylisochroman-1-yl)phenyl]acetic acid ethyl ester, described in Example 18, [p-(6,7-dimethoxy-1-methylisochroman-1-yl)phenyl]acetic acid, m.p. 149°–151° C., is obtained.

In the same manner but replacing the above corresponding ethyl ester with an equivalent amount of 6,7-dihydro-4-methyl-4H-thieno[3,2-c]pyran-4-acetic acid ethyl ester, described in Example 25, 6,7-dihydro-4-methyl-4H-thieno[3,2-c]pyran acetic acid, m.p. 89°–92° C., is obtained.

In the same manner but replacing the above corresponding ethyl ester with an equivalent amount of 6,7-dihydro-4-methyl-4-H-thieno[3,2-c]pyran-4-propionic acid methyl ester, described in Example 26, 6,7-dihydro-4-methyl-4H-thieno[3,2-c]pyran-4-propionic acid, m.p. 67°–68° C., is obtained.

In the same manner but replacing the above corresponding ethyl ester with an equivalent amount of 3,4-dihydro-1-methyl-1H-[1]benzoithieno[2,3-c]pyran-1-acetic acid ethyl ester, described in Example 31, 3,4-dihydro-1-methyl-1H-[1]benzothieno[3,2-c]pyran-1-acetic acid, m.p. 149°–152° C., is obtained.

In the same manner but replacing the above corresponding ethyl ester with an equivalent amount of 3,4-dihydro-1-methyl-1H-pyrano[4,3-b]benzofuran-1-acetic ethyl ester, described in Example 33, 3,4-dihydro-1-methyl-1H-pyrano[4,3-b]benzofuran acetic acid, m.p. 152°–154° C., is obtained.

In the same manner but replacing the above corresponding ethyl ester with an equivalent amount of 3,4-dihydro-1-methyl-1H-benzothieno[2,3-c]pyran1-acetic acid ethyl ester, described in Example 38, 3,4-dihydro-1-methyl-1H-benzothieno[2,3-c]pyran-1acetic acid, m.p. 166°–168° C., is obtained.

In the same manner but replacing the above corresponding ethyl ester with an equivalent amount of 4',9'-dihydrospiro[cyclohexane-1,1'(3'H)-pyrano[3,4-b]indole]-2-acetic acid ethyl ester, described in Example 50, 4',9'-dihydrospiro[cyclohexane-1,1'(3'H)-pyrano[3,4-b]indole]-2-acetic acid, m.p. 167°–170° C., is obtained.

In the same manner but replacing the above corresponding ester with an equivalent amount of 4',9'-dihydrospiro[cyclopentane-1,1'(3'H)-pyrano[3,4-b]-indole]-2-carboxylic acid ethyl ester, described in Example 51, 4',9'-dihydrospiro[cyclopentane-1,1'(3H)-pyrano[3,4-b]indole]2-carboxylic acid, m.p. 168°–170° C., is obtained.

In the same manner but replacing the above corresponding ester with an equivalent amount of 2,3,6,7,9,10-hexahydro-7-propyl-H-1H-cyclopenta[e]-pyrano[3,4-b]indole-7-acetic acid ethyl ester, described in Example 41, 2,3,6,7,9,10-hexahydro-7-propyl-1H-cyclopenta[3]pyrano[3,4-b]indole-7-acetic acid, m.p. 153°–155° C., is obtained.

In the same manner but replacing the above corresponding ester with an equivalent amount of 1,2,3,4,7,8,10,11-octahydro-10-methylbenzo[g]-pyrano[3,4-b]indole-10-acetic acid ethyl ester, described in Example 42, 1,2,3,4,7,8,10,11-octahydro-10-methylbenzo[g]pyrano[3,4-b]indole-10-acetic acid, m.p. 153°–155° C., is obtained.

In the same manner but replacing the above corresponding ester with an equivalent amount of 1,2,3,4,7,8,10,11-octahydro-10-propylbenzo[g]-pyrano[3,4-b]indole-10-acetic acid ethyl ester, described in Example 43, 1,2,3,4,7,8,10,11,-octahydro-10-propylbenzo[g]pyrano[3,4-b]indole-10-acetic acid, m.p. 104°–106° C, (also isolated as an ethyl acetate solvate, m.p. 78°–80° C), is obtained.

In the same manner but replacing the above corresponding ester with an equivalent amount of 1,5-dimethyl-1,3,4,5-tetrahydropyrano[4,3-b]indole-1- acetic acid ethyl ester, described in Example 44, 1,5-dimethyl-1,3,4,5-tetrahydropyrano[4,3-b]indole-1-acetic acid, m.p. 181°-182° C, after crystallization from benzene-hexane, is obtained.

In the same manner but replacing the above corresponding ester with an equivalent amount of 1-methy-1-isochromanacetic ethyl ester, described in Example 1, 1-methyl-1-isochromanacetic acid, m.p. 103°-105° C., is obtained.

In the same manner but replacing the above corresponding ester with an equivalent amount of 1,2-dihydro-4-methyl-4H-naphtho[2,1-c]pyran-4-acetic acid ethyl ester, described in Example 1, 1,2-dihydro-4-methyl-4H-naphtho[2,1 -c]pyran-4-acetic acid, m.p. 156°-158° C., is obtained.

The acids prepared by the procedure of this example exhibit antiinflammatory activity.

EXAMPLE 70

6,7-dimethoxy-1-methyl-4-oxo-1-isochromanpropionic acid

A solution of chromium trioxide (25.7 g) in a mixture of acetic acid (120 ml) and water (35 ml) is added dropwise to a solution of 6,7-dimethoxy-1-methylisochroman propionic acid (27.0 g), described in Example 16, in acetic acid (140 ml) keeping the temperature of the mixture below 20° C. The mixture is kept at room temperature for 1.5 hr. and then poured into water and extracted with chloroform. The extracts are thoroughly washed with water, dried and evaporated. The residue is crystallized from benzene to give the title compound, m.p. 172°-173° C.

In the same manner but replacing 6,7-dimethoxy-1-methylisochromanpropionic acid with an equivalent amount of 1-(4-biphenylyl)-6,7-dimethoxy-1-methyl-4isochroman, described in Example 19, 1-(4-biphenylyl)-6,7-dimethoxy-1-methyl-4-isochromanone, m.p. 170°-172° C., is obtained.

The two products prepared by the procedure of this example exhibit antibacterial activity.

EXAMPLE 71

N,N-Diethyl-2-{[(1-thienyl)ixochroman-6-yl]oxy}ethylamine

A mixture of 1-(2-thienyl)-6-isochromanol (8.0 g), described in Example 21, sodium hydride (1.85 g of a 50% suspension) and anhydrous benzene (100 ml) is heated under reflux for 1 hr. The mixture is then cooled to 40°C and a solution of diethylaminoethylchloride(-from 40 g of the hydrochloride) in anhydrous benzene (100 ml) is added dropwise. The mixture is heated under reflux overnight. The mixture is cooled, washed with water, dried and evaporated. The excess starting amine was removed under high vacuum to afford the title compound, nmr (CDCl$_3$) δ 4.00, and 6.00.

The corresponding oxalic acid addition salt of the title compound has m.p. 123°-127° C. and exhibits antibacterial activity.

EXAMPLE 72

1-Methyl-1-(3-pyridyl)-6-isochromanol acetate

A mixture of 1-methyl-1-(3-pyridyl)-6-isochromanol (5.0 g), described in Example 22, and acetic anhydride (50 ml) is heated on the steam bath for 4 hr. The mixture is poured upon ice, left at room temperature for 1 hr, rendered basic with sodium bicarbonate and then extracted with chloroform. The extracts are washed with brine, dried, evaporated, and the residue is crystallized from isopropanol to give the title compound, m.p. 113°-115° C.

The product of this example has antifungal activity.

EXAMPLE 73

6,7-Dihydro-N,N-dimethyl-4H-thieno[3,2-c]pyran-4-ethylamine

A mixture of 6,7-dihydro-4H-thieno[3,2-c]pyran-4-ethyl chloride (9.0 g), described in Example 24, 25% aqueous dimethylamine (40 ml) and dioxane (100 ml) is heated on the steam bath for 5 hr. The mixture is concentrated, diluted with water, made alkaline and extracted with chloroform. The extracted material is subjected to chromatography on neutral alumina. Elution with benzene, followed by mixtures of benzene and chloroform and finally chloroform affords the title compound, $\lambda_{max}^{EtOH}$ 233 nm (6900).

The corresponding oxalic acid addition salt has m.p. 116°-119° C.

In the same manner but replacing dimethylamine with an equivalent amount of N-methylpiperazine, 1-[2-(6,7-dihydro-4H-thieno[3,2-c]pyran-4-yl)ethyl]-4-methylpiperazine, $\lambda_{max}^{EtOH}$ 233 mμ (6780), is obtained the corresponding oxalic acid addition salt (dioxalate) thereof having m.p.236°14 237° C after recrystallization from water.

The two hydrochloric acid addition salts of this example exhibit antibacterial activate.

EXAMPLE 74

N,N-Diethyl-6,7-dihydro-4,4-dimethyl-4H-thieno[3,2-c]pyran-4-amine

A mixture of 4,4-dimethyl-6,7-dihydro-4H-thieno[3,2-c]pyran (16.8 g), described in Example 29, carbon tetrachloride (200 ml), N-bromosuccinimide (17.8 g) and benzoyl peroxide (100 mg) are heated under reflux until the starting material is consumed (2hr.). The mixture is filtered and the filtrate is evaporated (T<40° C) and diethylamine (50 ml) is added to the residue. The mixture is heated under reflux for 5 hr. and left overnight at room temperature. The excess amine is evaporated under reduced pressure and the basic product is isolated in the usual manner and purified by chromatography on neutral alumina. Elution with benzene, followed by chloroform yields the title compound, nmr (CDCl$_3$) δ 4.40 and 7.75.

The corresponding oxalic acid addition salt has m.p. 167°-170° C, after crystallization from chloroform and exhibits antibacterial activity.

EXAMPLE 75

3,4-Dihydro-N,N-diethyl-1H-[1]benzothieno[3,2-c]pyran-1-ethylamine

A mixture of 3,4-dihydro-1H-[1]benzothieno[3,2-c]pyran-1-ethyl chloride (12.0 g), described in Example 30, and diethylamine (80 ml) is heated under reflux for 48 hr. The excess amine is evaporated and the residue is dissolved in 2N HCl and washed with ether. The acidic solution is rendered basic and extracted with ether. These extracts are evaporated to yield the title compound, nmr (DMSO-d$_6$) δ 3.97 and 5.00.

The corresponding oxalic acid addition salt has m.p. 173°-175° C., after recrystallization from methanol.

In the same manner but replacing the diethylamine with an equivalent amount of dimethylamine, 3,4-dihydro-N,N-dimethyl-1H-[1]benzothieno[3,2-c]pyran-1- ethylamine, $\lambda_{max}^{EtOH}$ 231 nm (29,900), 262 nm (6760), 288 nm (2645), 297 nm (2655), is obtained; the corresponding oxalic acid addition salt thereof having m.p. 211°–213° c. after recrystallization from methanol-water.

The preceding two oxalic acid addition salts exhibit antibacterial activity.

EXAMPLE 76

3,4-Dihydro-N-methyl-1H-[1]benzothieno[2,3-c]pyran-1-methylamine

A mixture of formic acid (4.7 ml) and acetic anhydride (11.3 ml) is heated at 60° C for 2 hr. 3,4-Dihydro-1H-[1]benzothieno[2,3-c]pyran-1-methylamine (1.0 g), described in Example 34, is added at room temperature and the mixture is allowed to stand overnight. The mixture is poured on ice and extracted with chloroform. The extract is washed (brine), dried (MgSO$_4$) and evaporated to give 3,4-dihydro-N-formyl-1H-[1]benzothieno[2,3-c]pyran-1-methylamine, nmr (CDCl$_3$) δ 3.16 and 4.95.

The latter compound is dissolved in 200 ml of anhydrous tetrahydrofuran. The resulting solution is treated cautiously with lithium aluminum hydride (0.8 g). The mixture is heated under reflux for 4 hr. and then cooled and trated with water-tetrahydrofuran mixture. The mixture is filtered and the filtrate is evaporated to yield the title compound, nmr (CDCl$_3$) δ 4.02 and 5.42.

The corresponding hydrochloric acid addition salt of the title compound has m.p. 243°–245° C after crystallization from isopropanol. This salt has antibacterial activity.

EXAMPLE 77

3,4-Dihydro-N,N-dimethyl-1H-[1]benzothieno[2,3-c]pyran-1-methylamine

A mixture of 3,4-dihydro-1H-[1]benzothieno[2,3-c]pyran-1-methylamine (3.0 g), described in Example 34, formic acid (20 ml.) and formaldehyde (20 ml.) is heated on the steam bath overnight and then poured into ice-water. The mixture is made alkaline and extracted with chloroform. The extracts are washed, dried and evaporated to give the title compound, nmr (CDCl$_3$) δ4.60 and 5.55.

The corresponding hydrochloric acid addition salt of the title compound has m.p. 221°–223° C., after recrystallization from ethanol. This salt exhibits antibacterial properties.

EXAMPLE 78

3,4-Dihydro-N-methyl-1H-[1]benzothieno[2,3-c]pyran-1-ethylamine

A mixture of 3,4-dihydro-1H-[1]benzothieno[2,3-c]pyran-1-ethyl chloride (6.0 g), described in Example 35, and a saturated solution of methylamine in dry methanol (75 ml) is heated in a pressure bottle at 60° C. for 2 hr. The mixture is kept at room temperature for 2 days and then evaporated to dryness. The residue is dissolved in dilute hydrochloric acid and washed with ether. The free base is then liberated from the aqueous phase by the addition of 5% sodium hydroxide solution and extracted with ether. The extract is dried and concentrated to give the title compound, $\lambda_{max}^{EtOH}$ 231 nm (29,600), 261 nm (7580), 290 nm (2960), 298 nm (3140); nmr (CDCl$_3$) δ 2.25, 2.86, 5.00.

The corresponding hydrochloric acid addition salt of the title compound has m.p. 194° – 197° C., after recrystallization from methanol and exhibits antibacterial activity.

EXAMPLE 79

3,4-Dihydro-N,N-dimethyl-1H-[1]benzothieno[2,3-c]pyran-1-ethylamine

A mixture of 3,4-dihydro-1H-[1]benzothieno[2,3-c]pyran-1-ethyl chloride (6.0 g.), described in Example 35, dioxane (50 ml), and 40% aqueous dimethylamine (50 ml) is heated on a steam bath for 3 hr. The mixture is evaporated, diluted with 10% hydrochloric acid and washed with ether. The free base is then liberated from the aqueous phase by the addition of 5% sodium hydroxide soln. and taken up in ether. The ether phase is dried and concentrated to yield the title compound, nmr (CDCl$_3$) δ 2.80 and 4.13.

The corresponding hydrochloride addition salt has m.p. 219°–221° C., after crystallization from ethanol-ether and exhibits antibacterial activity.

In the same manner but replacing 3,4-dihydro-1H-[1]benzothieno[2,3-c]pyran-1-ethyl chloride with 3,4-dihydro-1-methyl-1H-[1]benzothieno[2,3-c]pyran-1-propyl chloride (see Example 36), or 3,4-dihydro-1-phenyl-1H-[1]benzothieno[2,3-c]pyran-1-propyl chloride (see Example 37), then 3,4-dihydro-N,N,1-trimethyl-1H-[1]benzothieno[2,3-c]pyran-1-propylamine, nmr(CDCl$_3$) δ 2.89 and 4.12, and 3,4-dihydro-N,N-dimethyl-1-phenyl-1H-[1]benzothieno[2,3-c]pyran-1-propylamine, nmr (CDCl$_3$) δ 3.07 and 3.99, are obtained, respectively.

The hydrochloric acid addition salt of 3,4-dihydro-N,N,1-trimethyl-1H-[1]benzothieno[2,3-c]pyran-1-propylamine has m.p. 218°–220° C., after recrystallization from ethanol-ether.

The maleic acid addition salt of 3,4-dihydro-N,N-dimethyl-1-phenyl-1H-[1]benzothieno[2,3-c]pyran-1-propylamine has m.p. 156°–158° C., after crystallization from ethanol.

The latter two hydrochloric acid addition salts exhibit antibacterial activity.

EXAMPLE 80

1,2,3,4,7,8,10,11-Octahydro-N,N,10-trimethylbenzo[g]pyrano[3,4-b]indole-10-acetamide 1,2,3,4,7,8,10,11-Octahydro-10-methylbenzo[g]pyrano[3,4-b]indole-10-acetic acid (4.5 g), described in Example 69, is suspended in anhydrous tetrahydrofuran (120 ml); triethylamine (4.2 ml) is added, followed by dropwise addition of ethyl chloroformate (2.14 ml) at −5° C. After stirring for 105 minutes at 0° C., the solution is added dropwise at 0° C., to a stirred solution of 40% aqueous dimethyl amine (62 ml). After 2 hr. at room temperature, the tetrahydrofuran is evaporated and water added. The mixture is extracted with chloroform, the organic solution washed with water (2 x), dried and taken to dryness to give the title compound, m.p. 176°–178° C., $\nu_{max}^{CHCl_3}$ 3360, 1630 cm$^{-1}$. This compound exhibits antibacterial activity.

EXAMPLE 81

10-[2-(Dimethylamino)ethyl]-1,2,3,4,7,8,10,11-octahydro-10-methylbenzo[g]pyrano[3,4-b]indole 1,2,3,4,7,8,10,11-Octahydro-N,N,10-trimethylbenzo[g]pyrano[3,4-b]indole-10-acetamide (5.1 g), described in Example 80, is dissolved in dry tetrahydrofuran (100 ml), lithium aluminum hydride (2.0 g) is added in portions and the reaction mixture is heated at reflux for 2 hr.

The excess reagent is decomposed by dropwise addition of water with stirring and cooling, additional tetrahydrofuran and MgSO₄ is added to the white precipitate. After stirring for 5 minutes the precipitate is collected and washed with tetrahydrofuran. The combined filtrates are taken to dryness to give the title compound, nmmr (CDCl₃) δ 1.62, 1.86, 2.72.

The corresponding maleic acid addition salt has m.p. 183°-185° C., and exhibits antibacterial properties of the title compound.

EXAMPLE 82

By following sequentially the procedures of Examples 80 and 81 but replacing 1,2,3,4,7,8,10,11-octahydro-10-methylbenzo[g]pyrano[3,4-b]indole-10-acetic acid with an equivalent amount of 1,5-dimethyl-1,3,4,5-tetrahydropyrano[4,3-b]indole-1-acetic acid, described in Example 69, 1-[2-(dimethylamino)ethyl]-1,5-dimethyl-1,3,4,5-tetrahydropyrano[4,3-b]indole, nmr (CDCl₃) δ 1.62, 2.15 and 4.12, is obtained; the corresponding oxalic acid addition salt thereof having m.p. 139° – 140° C., after crystallization from isopropanol. The latter salt exhibits antibacterial activity.

By following sequentially the procedures of Examples 80 and 81 but replacing 1,2,3,4,7,8,10,11-octahydro-10-methylbenzo[g]pyrano[3,4-b]indole-10-acetic acid and dimethylamine with equivalent amounts of 1,5-dimethyl-1,3,4,5-tetrahydropyrano[4,3-b]indole-1-acetic acid and diethylamine, respectively, 1-[2-(diethylaminoethyl]-1,5-dimethyl-1,3,4,5-tetrahydropyrano[4,3-b]indole, nmr (CDCl₃) δ 1.63, 3.65 and 4.05, is obtained; the oxalic acid addition salt thereof having m.p. 122° – 124° C., after crystallization from isopropanol. The latter salt exhibits antibacterial activity.

We claim:

1. A process for preparing a polyclclic heterocycle compound having a pyran ring which comprises reacting in the presence of a Friedel Crafts type catalyst a compound of the formula II:

B—CH₂CH₂OH (11)

wherein B is

with a compound of the formula III:

R¹—C—R² in which L and M each represent lower alkoxy or together represent the ethylenedioxy radical or oxo, and wherein R¹ is hydrogen, lower alkyl, phenyl or p-halophenyl, and R² is 2-furyl, 2-thienyl, 2-pyridyl, 3-pyridyl, 4-pyridyl; or R² is

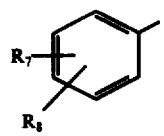

wherein R⁷ and R⁸ are the same or different and each represent halo, hydroxyl, carboxyl, carb(lower)alkoxy, or R¹ and R² together with the carbon atoms to which they are both joined to form a radical of the formula

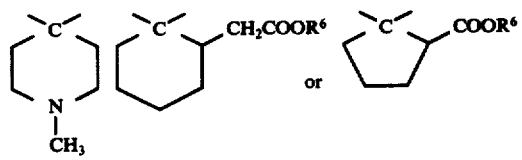

in which R⁶ is lower alkyl.

2. The process of claim 1 wherein said catalyst is selected from the group consisting of p-toluenesulfonic acid, phosphorus pentoxide, boron trifluoride, zinc chloride, hydrochloric acid or sulfuric acid.

3. The process of claim 1 wherein said catalyst is hydrogen chloride.

4. The process of claim 1 wherein the compound of formula 11 is reacted with the compound of formula 111 for a period of from about 10 minutes to about 60 hours, at a temperature ranging from about −20° C to the boiling point of the reaction mixture, and employing from about 0.01 to about 100 molar equivalents of the Friedel Crafts reaction catalyst.

5. The process of claim 1 wherein the compoud of formula 11 is reacted with the compound of formula 111 for a period of from about 10 minutes to about 60 horus, at a temperature ranging from about 20° C to the boiling point of the reaction mixture, and employing from about 0.01 to about 100 molar equivalents of the Friedel-Crafts reaction catalyst.

6. The process of claim 5 wherein B is

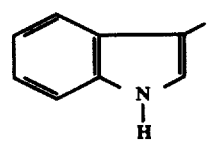

R¹ and R² together with the carbon atom to which they are both joined form a radical of the formula

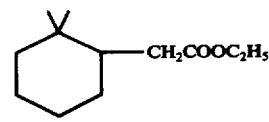

L and M together represent oxo, and the component of formula 111 is ethyl 2-cyclohexanone acetate.

7. The process of claim 5 wherein B is

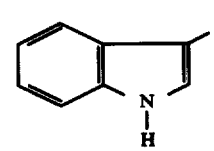

R¹ and R² together with the carbon atom to which they are both joined form a radical of the formula

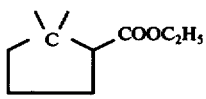

L and M together represent oxo, and the compound of formula III is ethyl 2-cyclopentanone carboxylate.

8. The process of claim 5 wherein B is

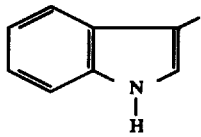

R¹ and R² together with the carbon atom to whch they are both joined form a radical of the formula

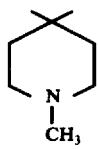

and the compound of formula III is 1-methyl-4-piperidone.

9. A process for preparing a polyclyclic heterocycle compound haing a pyran ring which comprises reacting in the presence of a Friedel Crafts type catylyst a compound of the formula II:

B—CH₂CH₂OH (II)

wherein B is

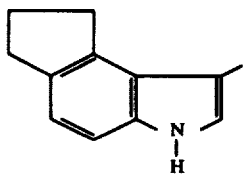

with a compound of the formula III:

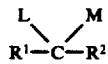

in which
R¹ is n—C₃H₇, R² is CH₂COOC₂H₅, and L and M taken together are oxo.

10. A process for preparing a polycyclic heterocycle compound having a pyran ring which comprises reacting in the presence of a Friedel Crafts type catylyst a compound of the formula II:

T—CH₂CH₂OH (II)

wherein B is

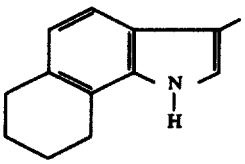

with a commpound of the formula III:

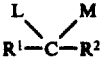

in which
R¹ is CH₃, or n—C₃H₇; R₂ is CH₂COOC₂H₅, and L and M taken together are oxo.

11. A process for preparing 1-acetyl-4',9'-dihydrospiro[piperidine-4,1'-(3'H)-pyrano[3,4-b]indole] which comprises reacting in the presence of a Friedel Crafts type catalyst a compound of the formula II:

B — CH₂CH₂OH (II)

wherein B is

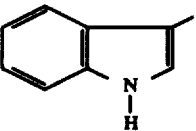

with 1-acetyl-4-piperidone.

* * * * *